United States Patent
Stewart

(10) Patent No.: US 8,774,908 B2
(45) Date of Patent: *Jul. 8, 2014

(54) SYSTEMS FOR DETECTING CARDIAC ARRHYTHMIAS

(75) Inventor: Donald-Bane Stewart, Edinburgh (GB)

(73) Assignee: Spacelabs Healthcare LLC, Snoqualmie, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/538,981

(22) Filed: Jun. 29, 2012

(65) Prior Publication Data

US 2013/0172765 A1    Jul. 4, 2013

Related U.S. Application Data

(63) Continuation of application No. 12/114,692, filed on May 2, 2008, now Pat. No. 8,233,973.

(51) Int. Cl.
*A61B 5/0456* (2006.01)

(52) U.S. Cl.
USPC .......................................................... 600/516

(58) Field of Classification Search
USPC ................................................. 600/516, 518
See application file for complete search history.

(56) References Cited

U.S. PATENT DOCUMENTS

| | | | |
|---|---|---|---|
| 6,480,733 B1 * | 11/2002 | Turcott | 600/516 |
| 6,490,479 B2 | 12/2002 | Bock | |
| 6,519,490 B1 | 2/2003 | Wiesel | |
| 6,597,943 B2 | 7/2003 | Taha et al. | |
| 6,871,089 B2 | 3/2005 | Korzinov et al. | |
| 6,922,584 B2 | 7/2005 | Wang et al. | |
| 7,020,514 B1 | 3/2006 | Wiesel | |
| 7,031,765 B2 | 4/2006 | Ritscher et al. | |
| 7,120,485 B2 | 10/2006 | Glass et al. | |
| 7,146,206 B2 | 12/2006 | Glass et al. | |
| 7,194,300 B2 | 3/2007 | Korzinov | |
| 2006/0084883 A1 | 4/2006 | Linker | |

OTHER PUBLICATIONS

Logan B, Healey J., "Robust Detection of Atrial Fibrillation for a Long Term Telemonitoring System," Computers in Cardiology 2005; 32:619-622.

Physician's Operation Manual, King of Hearts Express AF, Feb. 2004, http://www.instromedix.com/pdf/products/cardiac/KOHEX_AF_physician.pdf.

* cited by examiner

*Primary Examiner* — Amanda Patton
(74) *Attorney, Agent, or Firm* — Novel IP

(57) ABSTRACT

A system for calculating a variability value that is indicative of AF by obtaining a signal sequence of a plurality of RR intervals by monitoring electrical activity of a patient's heart. Each RR interval is converted into an instantaneous heart rate value and sorted into ascending order. The difference between each successive heart rate is calculated, discarding the two largest differences. The variability value is calculated by adding the retained differences.

31 Claims, 3 Drawing Sheets

SYSTEMS FOR DETECTING CARDIAC ARRHYTHMIAS

CROSS-REFERENCE

The present application is a continuation of U.S. patent application Ser. No. 12/114,692, filed on May 2, 2008 now U.S. Pat. No. 8,233,973 and entitled "Methods for Detection of Cardiac Arrhythmias.

FIELD

The present application relates generally to methods for detecting cardiac arrhythmia. Specifically, the present application relates to methods for detecting atrial fibrillation and atrial flutter. More specifically, the present application relates to improved methods for detecting atrial fibrillation and atrial flutter using local heart rate measurements that take into account common confounding ectopy. More particularly, the present application relates to improved methods for detecting atrial fibrillation and atrial flutter that employ measurements of RR or NN variability while avoiding the effects of single-focus ectopic arrhythmia.

BACKGROUND

Atrial fibrillation and atrial flutter are types of cardiac arrhythmia (hereinafter, collectively referred to as "AF") or abnormal heart rhythm that are difficult to automatically identify. The difference between atrial fibrillation and atrial flutter is mainly one of atrial rate, atrial flutter being the faster of the two.

By way of background, FIG. 1 illustrates a typical electrocardiogram (ECG) tracing of a normal heartbeat (or cardiac cycle), showing the electrical conduction system of the heart. In cardiac practice, heartbeats are named according to the initial source of the heartbeat. The normal beating of the heart is known as "sinus rhythm", because the normal heart beat is initiated by a small area of specialized muscle in the atria referred to as the sinoatrial (SA) node (or more commonly, the "sinus node"). When electrical activity is spontaneously generated by the sinus node, the electrical impulse is propagated throughout both the right atrium and left atrium, stimulating the myocardium of the atria to contract. When the atria contract, blood is pumped from the atria of the heart to the lungs and then back into the ventricles.

Referring now to FIG. 1, the conduction of the electrical impulse throughout the atria is seen on the ECG as P-wave 101. Thus, the P-wave 101 represents the electrical potential generated by atrial muscle cell depolarization as the heart's atrial chambers contract.

The spread of electrical activity through the ventricular myocardium causes the ventricles of the heart to contract. When the ventricles contract, the blood in the ventricles is pumped at high pressure around the body (and eventually back to the atria). The conduction of the electrical impulse throughout the ventricles is seen on the ECG as the QRS complex 102 on the ECG. More specifically, the QRS complex 102 represents the electrical potential generated by ventricular muscle cell depolarization as the heart's ventricular chambers contract.

The "AV node" is a specialized section of the myocardium located between the atria and the ventricles. The AV node functions as a critical delay in the conduction system. In order for the heart to work well, the heart must first pump blood from the atria to the ventricles (via the lungs, where the blood becomes oxygenated). Once this occurs, the ventricles then pump the oxygenated blood throughout the body. The AV delay allows the atria to fill the ventricles with blood before the ventricles are pumped. If the ventricles are pumped prior to being filled with blood from the lungs via the atria, the ventricular pump action would oppose the movement of blood from atria to ventricles and reduce the pressure of the blood moving from the ventricles to the rest of the body. The delay in the AV node is observed as the PR segment 105 on the ECG.

The last event of the cycle is the repolarization of the ventricles, represented on the ECG by T-wave 103. The T-wave 103 represents the electrical potential generated as the ventricles of the heart recover (or repolarize) from a state of depolarization after the QRS complex has occurred. It should be noted that there is an equivalent repolarization wave for the P-wave, occurring during the PR segment and traversing somewhat into the QRS complex: however, from a surface ECG, this repolarization signal is typically too small to be seen.

Other characteristic features of sinus rhythm include a PR-interval 104, ST-segment 106 and QT-interval 107. The PR-interval 104 is measured from the beginning of the P-wave 101 to the beginning of the QRS complex 102. The ST-segment 106 is measured from the end of the QRS complex 102 to the beginning of the T-wave 103. The QT-interval 107 is measured from the beginning of the QRS complex 102 to the end of the T-wave 103. These generic features of sinus rhythm serve as hallmarks for comparison with normal ECGs.

FIG. 2 illustrates two successive cycles of sinus rhythm. The distance between the R waves of two successive cardiac cycles 200 is known as the RR interval 201. While one would ideally measure the 'ventricular rate' as the QQ interval 202 (which is the interval from QRS onset to the next QRS onset), in practice, the RR interval is used as the measurement of ventricular rate, due to the practical difficulty of reliably measuring the small, inconsistently sized and inconsistently occurring Q-wave. In the case of sinus rhythm, when successive beats are both "Normal", the RR interval of such a cycle is often referred to as an "NN interval". The NN interval 203 thus reflects the underlying sinus rhythm. The distance between the on-set of successive P waves is known as the PP interval (or atrial rate) 204.

As shown in FIGS. 1 and 2, the five distinct waves (P, Q, R, S and T) present in a single beat of the heart in sinus rhythm, along with the characteristic segments and intervals (such as PR, ST, QT, and RR) between two cardiac cycles, all occur in a specific order with an expected range of relative sizes. While there is a significant range within which variations in rhythm are considered normal, anything that deviates from sinus rhythm by more than a certain amount may be indicative of a heart condition.

As mentioned above, the normal beating of the heart is known as "sinus rhythm". When areas of the heart other than the sinus node initiate a heartbeat, they are generally referred to as "ectopic beats" since they occur 'out-of-place' with respect to sinus rhythm. More specifically, ectopics are named according to the area of the heart (or focus) that initiated the heartbeat, and often have subsidiary information regarding whether these heartbeats are at a notably different heartrate to that of the current sinus rate or not. For example a heartbeat having an atrial origin, excluding the sinus node, may be referred to as an "atrial ectopic". Were this heartbeat to occur faster than the current sinus rate, it would be termed a "premature atrial ectopic"; were it to occur slower than the current sinus rate, it would be termed an "atrial escape beat".

Similarly, for ventricular activity, the terms "ventricular ectopics", "premature ventricular ectopics" (or "complexes", thus often called "PVCs"), and "ventricular escape beats" are used.

Even the aforementioned AV node can initiate heartbeats—referred to as junctional ectopics—though it is usual practice to group these together with atrial ectopics under the umbrella-name "supra-ventricular ectopics" or SVEs (so called as the atria and AV node are both physically 'above' the ventricals).

It should be noted that almost any area of the heart can generate a heartbeat as a back-up mechanism for when the sinus node does not start a heartbeat when it should. Escape ectopics are a manifestation of the back-up mechanism working correctly and are thus not themselves a problem but rather indicate that a problem has occurred with the sinus node. However, premature ectopics occur before the sinus node and override the correct sinus beat, thus indicating a problem with the area of the heart that prematurely generated an 'erroneous' back-up beat.

Most people spend most of their time in sinus rhythm, with some infrequent ectopics occurring. When ectopics become frequent, it is usually caused by a specific part of the heart causing a problem. For example, a specific area of the heart may be implicated if a particular premature SVE or PVC becomes common, sometimes occurring in lengthy patterns such as ventricular bigeminy (such as where a sinus beat is followed by a PVC and this pattern then repeats over and over).

Atrial fibrillation and atrial flutter are related types of cardiac arrhythmia (or abnormal heart rhythm) where rather than just a specific problem area of the heart causing a specific type of ectopic, the entire atria starts to generate electrical impulses that can initiate a heartbeat. In a sense, AF is effectively caused by hundreds of different atrial ectopics, all in competition with each other, overwhelming the sinus node. Because the area of the heart that generates the next heartbeat is not fixed, the heart rate of the next heartbeat is also not fixed and thus a highly chaotic sequence of heartbeats is observed. In addition, several P-waves per QRS complex are observed, as the ventricles cannot respond to every P-wave the atria generate. As the P-waves originate from different parts of the atria, their shapes are not constant, so the collection of high-rate P-waves between QRS complexes in AF can often resemble little more than a messy line on an ECG. Thus, in AF, the electrical impulses that are normally generated by the SA node are replaced by disorganized activity in the atria. In the case of atrial flutter, some level of organization can sometimes occur in the atria, with the multiple-P-waves starting to look like a train of "saw-tooth" waves at a very high atrial rate.

There are instances of AF however, where the ventricular rate is not chaotic. This happens for one of two reasons: either the ventricular rate has reached the maximum possible rate and thus, responds to whatever random P-wave that occurs at a time which allows it to continue at this rate, or very rarely, "AV dissociation" occurs, where the communication between the atria and the ventricles has completely broken down and which typically requires pacemaker implantation.

Prior art methods have attempted to detect AF events based on either the variability of ventricular rate and/or measurements of the atrial rate. However, conventional prior art methods for detecting AF using measurements of atrial rate are lacking, in that atrial rate is a difficult parameter to measure due to the small size of P-waves and their inconstant morphology during AF events. Typically, only internal pacemaker or ICD devices attempt to measure atrial rate, using a sensor that is physically attached to the atrium in order to achieve this. Other methods for atrial rate determination are notoriously unreliable in an ambulatory setting, and are thus rarely attempted.

Further, while there is a significant amount of prior art relating to methods for detecting AF, they all tend to suffer the same problem, specifically, that commonly occurring non-AF arrhythmia is mistaken for AF by the detection method.

Specifically, in prior art methods for detecting AF that are based on RR variability measurements, false positive AF detections are often caused by non-AF ectopics as these also cause significant RR variability. Much of the prior art assumes that non-AF ectopics do not occur over long durations of time. However, this is not the case for certain patterns of ectopics, such as atrial bigeminy, ventricular bigeminy or intermittent heart block, which can and do occur for extended periods of time.

For example, Hewlett Packard Labs (HPL) has developed a method for detection of atrial fibrillation for a long-term telemonitoring system. (Computers in Cardiology 2005; 32:619-622). In particular, HPL presents a "method to automatically detect Atrial Fibrillation (AF) for ambulatory monitoring . . . [with an] approach based on the variance of R-R intervals . . . " More specifically, the HPL method "uses the morphology-independent QRS detector wqrs to compute R-R intervals and variance and then smooth the resulting classifications for further robustness." This system, however, effectively treats all long-term non-sinus behavior as atrial fibrillation and thus fails to take into consideration long-term confounding events. It is also limited to detecting AF events having a duration of two minutes or longer.

U.S. Pat. No. 6,871,089 (the "'089 patent"), assigned to Card Guard Technologies, Inc., describes "a method of detecting atrial fibrillation in a patient, the method comprising: measuring R-R intervals between a plurality of QRS complexes of the patient, including present and preceding QRS complexes; forming a first ratio by dividing an R-R interval into another R-R interval in which one R-R interval is the present interval and one R-R interval is a preceding interval; forming a second ratio by dividing an R-R interval into another R-R interval in which one R-R interval is the present interval and one R-R interval is a preceding interval different from the preceding interval used in the first ratio; averaging a plurality of first ratios to form a first average; averaging a plurality of second ratios to form a second average; analyzing the difference between the first and second averages; [and] comparing the difference between the averages to a threshold to determine if an atrial fibrillation exists in the patient." Thus, the '089 patent calculates ratios of the current R-R interval to previous R-R intervals and compares those ratios to a validating threshold. This method is targeted towards avoiding variability caused by PVCs, bigeminy and trigeminy, however, adversely impacts the variability measurement within true AF, which on a short time-scale (the two or three intervals as described in this patent) will often exhibit interval changes similar to such arrhythmia, and can thus be similarly suppressed.

In another example, United States Patent Publication Number 2006/0084883, assigned to the University of Washington, discloses "a method for detection of an arrhythmia, the method comprising: determining number of heart beat intervals; determining an instantaneous heart rate for each of the heart beat intervals; determining the variability of the instantaneous heart rates compared to a mean of the number of instantaneous heart rates; determining a non-linear value that represents the variability of the instantaneous heart rates; and detecting the arrhythmia by comparing the non-linear value with a predetermined threshold." Specifically, the disclosed methods "are based on the variability of RR intervals." The methods of the patent application disclosed herein do aim to exclude some ectopy by applying non-linear filtering to the sequence of successive differences of RR intervals. However, filtering the differences between successive RR intervals assumes that there are some intervals that can be valid indicators of non-ectopic transition intervals. For arrhythmia such as bigeminy, this assumption is not correct and this method will measure high variability, and thus detect AF, where such confounding arrhythmia is present. Thus, the method can only detect isolated non-AF arrhythmia—longer-term patterns of ectopic states, such as bigeminy or intermittent heart block, will inevitably cause false positive AF detection.

U.S. Pat. No. 6,490,479, assigned to GE Medical Systems Information Technologies, Inc., describes "a method of detecting an arrhythmia from ECG information, the method comprising: classifying the ECG information; determining intervals between recurring events in the ECG information; determining a probability that an irregular condition exists based on classifying the ECG information and determining an interval between recurring events; generating a state variable based upon the determined probability; generating a contextual output based on similarities in intervals between recurring events; determining the presence of a P-wave in the ECG information; generating a detection output based on determining the presence of a P wave; and determining the existence of the irregular condition based on the state variable, the contextual output, and the detection output." The system and method described relies upon reliable P-wave detection, a process that is notoriously unreliable when performing non-invasive heart monitoring as described above.

U.S. Pat. No. 6,519,490, (the "'490 patent") assigned to Wiesel, describes "a method of detecting irregular cardiac activity, said method comprising the steps of (a) determining a plurality of time intervals each corresponding to a respective time period between successive ones of a sequence of heartbeats; (b) determining a mean and a standard deviation of said plurality of time intervals; (c) selecting, when a quotient formed by dividing said standard deviation by said mean has a value greater than or equal to a threshold value, a shortest one of said plurality of time intervals and a succeeding time interval that immediately follows said shortest one; (d) determining, when said succeeding time interval has a value less than or equal to said mean, that said cardiac activity is irregular." The '490 patent effectively locates regions of the heartbeat signal that have irregularity, then performs a simple check if the irregularity is caused by an isolated PVC or SVE: if so, it is excluded, if not, an "irregular heart rate" is detected, which can be loosely associated with AF. Thus, the '490 patent does not specifically detect AF, but rather "irregular heart rate" regions. Similarly, U.S. Pat. No. 7,020,514, also assigned to Wiesel, does not differentiate the different types of irregular heartbeats and only determines a pulse rate pattern that indicates a possible AF event.

In addition, other prior art conventional methods of analyzing RR interval patterns to detect AF events art are illustrated in the following United States Patents. Specifically, U.S. Pat. No. 6,922,584 describes a method wherein RR variability is essentially compared to a heart-rate-dependant threshold to detect AF. Further, U.S. Pat. No. 7,031,765 is directed towards clustering analyses of RR interval (or ΔRR interval) scatter plots, which require a significant number of values to create, and is thus limited to detecting long AF events only. Still further, U.S. Pat. No. 7,120,485 (and similarly, U.S. Pat. No. 7,146,206) describes a method that uses ΔRR histograms and compares the histograms to a set of pre-generated template AF histograms to identify AF, requiring a significant number of values to build reliable histograms and thus is limited to detecting long AF events only. U.S. Pat. No. 7,194,300 uses a technique where certain thresholds of RR variability are pre-determined, and only RR variability between these thresholds (i.e. neither very low, nor very high) is considered 'relevant' to AF, with other variability being deemed to be characteristic of non-AF behavior. Thus, AF events are defined over regions where some weighting function of each RR interval's relevance (or lack thereof) meets some defined criteria.

U.S. Pat. No. 6,597,943, assigned to GE Medical Systems Information technologies, discloses "a method and apparatus for differentiating among atrial-flutter, atrial-fibrillation and other cardiac rhythms [that] includes the steps of estimating spectral entropy of atrial cardiac activity from an electrocardiogram of a patient and determining that the patient has atrial fibrillation when the spectral entropy is greater than a predetermined value. The method involves determining an average temporal distance between successive R-waves identified within the QRS complex of the heartbeat of the patient over the sampling interval; forming a template of the QRS complex and T-wave by averaging respective sample values ahead of and behind the identified R-wave." This method is directed towards removing the QRS and T-wave from the ECG signal, and then performing an analysis on the remaining atrial ECG signal. Due to the low signal strength of P-waves and the irregularity of QRS and T-waves, this method requires high quality, low noise ECG signals and is not well suited to ambulatory measurement where QRS and T-wave variability is significantly increased with respect to resting ECG measurements.

As discussed above, conventional prior art techniques take advantage of high RR variability to detect AF. However, most non-AF types of heart arrhythmia also generate high RR variability and thus, confound the use of high RR variability as a means to detect AF.

More specifically, the prior art based on RR variability uses a direct analysis of the variability of sequential RR intervals, thus assuming that in the sequence of RR intervals, there exists some RR variability that is not dominated by non-AF ectopy. However, for longer-term patterns of ectopic states, such as atrial bigeminy, ventricular bigeminy or intermittent heart block, which can and do occur for extended periods of time, this assumption is not the case and false positive AF detections will result.

What is therefore needed is a method for detecting AF events that advantageously analyzes the RR interval states rather than a sequence of RR interval differences.

What is also needed is a method for detecting AF events that obtains a high variability measurement for AF but does not suffer a high measurement for the confounding ECG abnormality case.

SUMMARY

It is an object of the present application to provide systems and methods for calculating a variability value that is indicative of AF using a sequence of RR intervals, comprising the steps of obtaining a signal sequence comprising a plurality of RR intervals wherein said signal sequence is obtained by monitoring electrical activity of a patient's heart; converting each RR interval in said sequence into an instantaneous heart rate value; sorting said instantaneous heart rate values into ascending order; calculating the difference between each successive heart rate; discarding the two largest differences generated in the previous step; and calculating a variability value by adding the retained differences. The systems comprises a non-volatile computer medium that store a plurality of programmatic instructions which, when executed, perform the methods described herein.

One of ordinary skill in the art would appreciate that the RR interval sequence is simply formed by timing the intervals between successive beats of a patient's heart. Thus any device that can measure when a heat beat occurs, such as, but not limited to: an auscultation or phonocardiogram device; a blood pressure, velocity or oxygenation-sensing device; a trans-thoracic-impedance device or an ultrasonic heart movement/deformation measurement device, could be used to generate the RR interval sequence in place of the above-described embodiment which monitors the electrical activity of a patient's heart to generate the RR interval sequence.

Further, the method of the present invention comprises the steps of segmenting said RR interval sequence into a plurality of segments and generating a variability value for each said segment. Still further, the method of the present invention comprises the step of filtering said generated variability value for at least one segment using previous and/or successive segment variability values, wherein such filtering is implemented by a 7-sample median filter in the described embodiment.

Still further, it is an object of the present invention to compare the at least one said variability value to at least one threshold, including an AF detection threshold or an AF start/end threshold, flagging a corresponding segment as 'probably containing AF' when said detection threshold is exceeded, detecting an AF event when a pre-determined number of consecutive segments are flagged as 'probably containing AF' and flagging a corresponding segment as 'AF extension permitted' when said start/end threshold is exceeded. In addition, once an AF event has been detected, previous and/or following segments are tested for the AF extension permitted flag and, if found, the detected AF event is extended to include said segment(s).

In one embodiment of the present invention, RR intervals shorter than 180 milliseconds or longer than 2 seconds are discarded from the variability calculation.

In another embodiment of the present invention, the variability value is reduced by halving the variability value if the sequence contains no heart rate interval greater than a heart rate threshold. In one embodiment of the present invention, the heart rate threshold is 60 beats per minute.

In another embodiment of the present invention, the variability value of the sequence is limited if the sequence is identified as containing a heart rate trend, wherein the heart rate trend is identified by: for each instantaneous heart rate of an RR interval, if the heart rate is significantly greater or less than the previous interval heart rate, define the start of a trend. A trend is determined to persist until an RR interval with a significant heart-rate change in an opposite direction is detected.

In one embodiment, once a new trend is determined on a RR interval, all intervals in a previous trend are flagged as being of the previous trend type.

In one embodiment, each RR interval in a trend is flagged as being a member of a long heart rate if a consecutive number of RR interval trend flags exceeds a long heart rate threshold. In another embodiment, each RR interval in a trend is flagged as being a member of a short heart rate if a consecutive number of RR interval trend flags exceeds a lower short heart rate threshold. In another embodiment, each RR interval in a trend is flagged as being not trended if no threshold conditions apply.

In another embodiment, for a plurality of RR intervals, trend flags are tested to establish whether said plurality is dominated by heart trend behavior. In one embodiment, the testing is performed by assigning each long heart rate trend flag a count, assigning each short heart rate trend flag a count less than said count of the long heart rate trend flag, and assigning each non trend flag a count less than said count of the short heart rate trend flag. Further, in one embodiment, an average of said long heart rate trend count, short heart rate trend count, and non-trend count is taken. In one embodiment, if said average is below a first threshold, said plurality of RR intervals is determined to have no trend. In another embodiment, if said average is greater than a second threshold, said plurality of RR intervals is determined to have a strong trend. In yet another embodiment, if said average is between said first and said second thresholds, said plurality of RR intervals is determined to have an unknown trend.

It is another object of the present invention to validate each detected AF event, by assigning individual trend flags within that event, summing individual trend flags, and discarding the AF event as false detection where the average count over the AF event is greater than a predefined threshold.

It is still a further object of the present invention to provide a method for calculating a variability value that is indicative of AF using a sequence of NN intervals, comprising the steps of obtaining a signal sequence comprising a plurality of NN intervals wherein said signal sequence is obtained by monitoring electrical activity of a patient's heart; converting each NN interval in said sequence into an instantaneous heart rate value; sorting said instantaneous heart rate values into ascending order; calculating the difference between each successive heart rate; discarding the two largest differences generated in the previous step; and calculating a variability value by adding the retained differences.

BRIEF DESCRIPTION OF THE DRAWINGS

These and other features and advantages of the present invention will be appreciated, as they become better understood by reference to the following Detailed Description when considered in connection with the accompanying drawings, wherein.

DETAILED DESCRIPTION OF THE INVENTION

Figure 1:
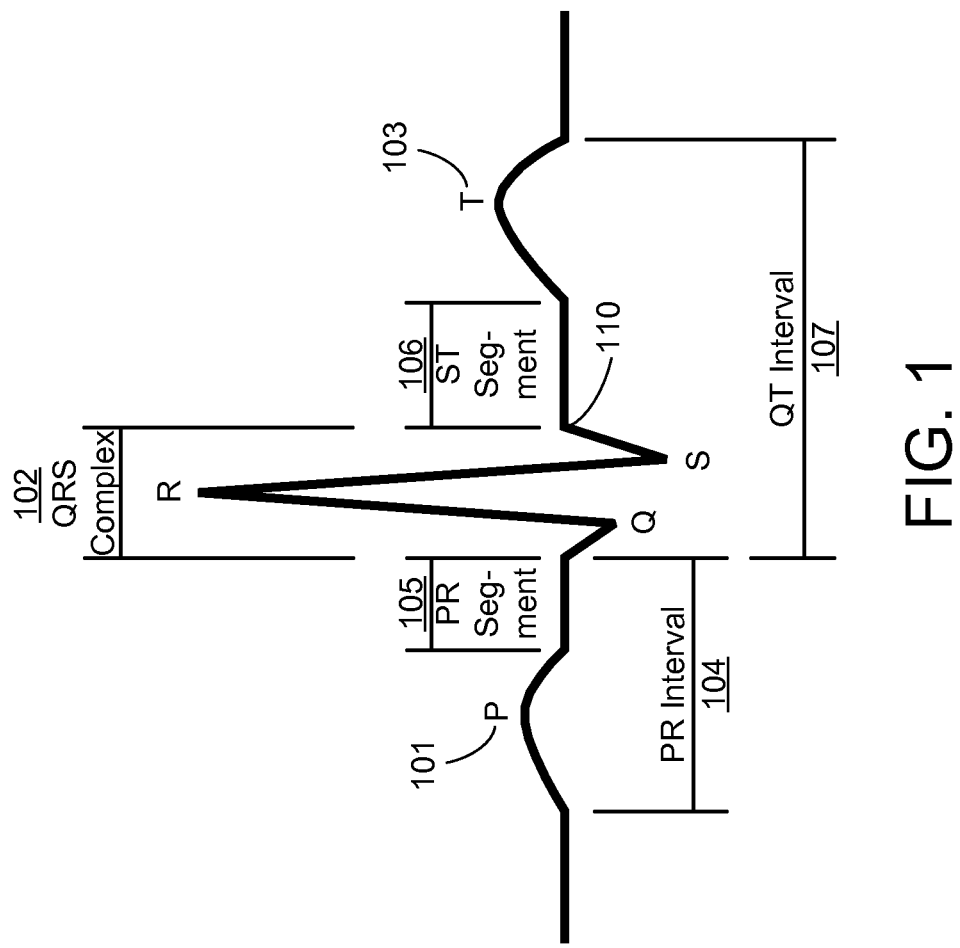
FIG. 1 is an illustration of a normal heartbeat (sinus rhythm) ECG waveform.
Figure 2:
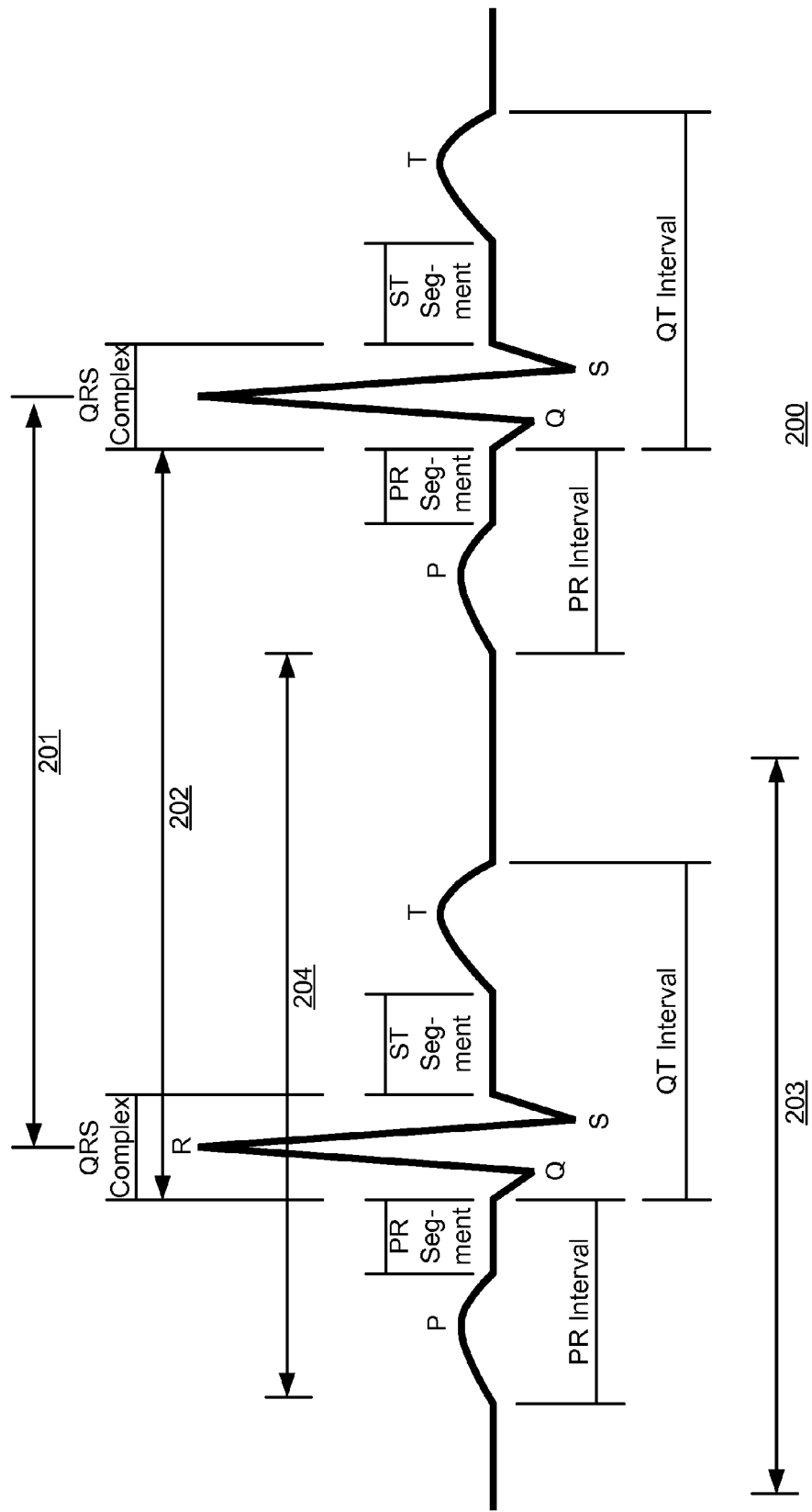
FIG. 2 is an illustration of two successive normal heartbeats in an ECG waveform, further illustrating the RR interval and PP interval.

The present invention is directed towards a method for detecting AF events from a sequence of heartbeat measurements where the origin of each heartbeat is not known, as is often the case with basic monitoring equipment, such as, but not limited to: heart rate monitors; event recorders; implantable pacemakers; and non-ECG heart rate measurement devices. The present invention is also directed towards transforming instantaneous heart rate signals into an AF output.

The vast majority of 'confounding ECG abnormalities' (i.e. non-AF ectopics that are falsely identified as AF) are caused by extended arrhythmias involving a combination of the sinus node and a single ectopic focus. Since successive heartbeats from the same focus, whether sinus or ectopic, typically have a low rate variability, the source of confounding variability occurs when switching from one state to another.

Depending on the switching pattern between these two foci, four groups of RR intervals are possible: the sinus-to-sinus group; ectopic-to-ectopic group; sinus-to-ectopic group and ectopic-to-sinus group. RR intervals can thus be assigned to specific groups, according to the types of heartbeats that surround the RR interval. For example, when two consecutive heartbeats surrounding an RR interval are of sinus origin, the RR interval belongs to the sinus-to-sinus group, often referred to as an NN interval (or sinus rate). As discussed, the variability within the sinus-to-sinus group and the ectopic-to-ectopic group is relatively small (similar to that of sinus rate itself). As the RR interval variability within each group (the intra-group variability) is typically much smaller than the difference in RR intervals between these groups (the inter-group variability), most of the variability measured is caused by inter-group variability: i.e. the transitions between the four groups, not the variability within them.

Between these groups, there are only two inter-group transitions: sinus-to-ectopic and ectopic-to-sinus. For most confounding ECG abnormalities, the sinus-to-ectopic interval will be shorter than sinus rate, as the confounding ectopic focus is likely a premature ectopic. When a sinus beat follows an ectopic beat, a heart rate longer than either sinus-to-sinus or ectopic-to-ectopic often occurs, either due to blocked AV conduction or atrial re-entry. This long interval is known as a 'compensatory' or 'partially compensatory' pause. Typically PVCs will show a near-full compensatory pause, while SVEs only exhibit a partially compensatory pause or revert to sinus rate immediately without showing any pause at all.

While each group could have its own unique associated RR interval, in practice the RR intervals of the ectopic-to-ectopic and sinus-to-ectopic groups are normally very similar, and thus only three different groups of RR intervals are typically observed.

The present invention is thus directed towards taking the RR intervals and sorting them according to RR interval length, obtaining the following ordering, as described above: firstly, a mix of all the sinus-to-ectopic and ectopic-to-ectopic intervals; secondly, all the sinus-to-sinus intervals; and finally all the ectopic-to-sinus intervals. Thus, the sorting process of the present invention effectively places each interval alongside those of the same group (the mixing of the first two groups is irrelevant as their RR groups are very similar, as discussed previously). However, it is not known at this point where the transitions between one group and another lie in this sorted sequence.

The method then measures the successive differences between each RR interval in the sorted list. The two largest difference values will correspond to a) the longest sinus-to-ectopic or ectopic-to-ectopic to the shortest sinus-to-sinus and b) the longest sinus-to-sinus to the shortest ectopic-to-sinus. Thus, the two largest differences always contain the inter-group variability.

The method of the present invention is further directed towards excluding the two largest differences, wherein the remaining variability is then representative of intra-group variability only. Hence this method of variability measurement of the present invention avoids undue influence caused by a single ectopic state, even when occurring in a long extended (and unknown) pattern.

AF, however, is an arrhythmia where every beat is effectively a different atrial ectopic, and therefore, every heartbeat forms its own RR group (except where the RR intervals happen to be similar by coincidence alone). Applying the same processing of sorting RR intervals, finding the two largest differences therein and excluding them, does not exclude all inter-group variability, as every difference value corresponds to a different inter-group transition. Thus, variability remaining after excluding the largest two differences still measures inter-group variability and, as a result, still obtains a high value.

Thus, by analyzing the RR interval states, a method unique to the present invention, rather than a sequence of RR interval differences as in conventional prior art methods, the calculation method of the present invention obtains a high variability measurement for AF but does not suffer a high measurement for the confounding ECG abnormality case.

The present invention is thus directed towards using a variability measurement that requires more than three different states to generate a significant variability measurement. As common ECG abnormalities only have two or three states present, the measurement of the present invention therefore suppresses confounding variability from said confounding ECG abnormalities. This is achieved by excluding a specific number of state transitions (or inter-group changes) such that sufficient state transitions are discarded to suppress said common ECG abnormalities, but for AF, where every interval is a state transition, AF still generates a significant variability measurement.

Thus, the present invention is directed towards a method of detecting AF with a lower false positive rate than that associated with prior art in the presence of common ECG abnormalities. The present invention has been evaluated on the industry standard database, the MIT-Atrial Fibrillation database, using the typical twin statistical measures of Duration Sensitivity ("DSe": the percentage of true AF that was detected) and Duration Positive Predictivity ("D+P": the percentage of detected AF that was true). Noting that AF events less than 20 seconds long were ignored, the present invention achieved DSe 99% and D+P 98.5%. These compare very favorably to the published statistics available for the prior art device "King of Hearts—Express AF" that, when ignoring AF events less than 30 seconds, are reported as DSe 79% and D+P 70%. Note that the higher threshold for excluding very short AF events used by the King of Hearts should improve these measurements rather than degrade them: thus the King of Hearts results are advantageously biased in this direct comparison. This information is excerpted from http://www.instromedix.com/pdf/products/cardiac/KOHEX_AF_physician.pdf, page 57, which is herein incorporated by reference. It should be noted herein that some comparisons with other devices are not available due to lack of published data or, more commonly, that the published data cannot be used for direct comparison due to excessive pre/post-processing.

The present invention is directed toward multiple embodiments, according to the data processing capabilities and resources available in the specific embodiment. Reference will now be made in detail to specific embodiments of the invention. Language used in this specification should not be interpreted as a general disavowal of any one specific embodiment or used to limit the claims beyond the meaning of the terms used therein.

One of ordinary skill in the art would appreciate that the features described in the present application are enabled by source code, compiled into an executable application and executing on a computer. The computer can be any type of computing device, such as, but not limited to: a laptop; personal computer; personal data assistant; cell phone; server; embedded processor; DSP chip or specialized medical device. Additionally, the programmatic code can be compiled (whether that be pre-compiled or compiled "just-in-time") into a single application executing on a single computer, or distributed among several different computers operating locally or remotely to each other.

As mentioned above, the present invention is directed towards use with basic patient monitoring equipment, including, but not limited to: heart rate monitors; event recorders; implantable pacemakers and non-ECG heart rate measurement devices. More specifically, the present invention is directed towards use with systems and apparatuses for obtaining measurements of at least one of electrical activity; acoustic activity; trans-thoracic impedance; blood pressure; blood velocity; blood oxygenation; heart movement and/or deformation. It should be understood by those of ordinary skill in the art that the measurements of a patient's heart may be obtained from these devices via several different methods, including but not limited to: direct connection via electrical wiring or via wireless transmission (for example from implantable measurement devices).

In one preferred embodiment, the present invention is directed towards measuring RR variability using the method described in the steps below and shown in FIG. 3. As mentioned above, intra-group variability can only be assumed to be low over short-term timescales. Thus, the method of the present invention first begins, in step 301, by segmenting the full ventricular heart rate sequence (or RR interval sequence). Each segment must be long enough to contain sufficient RR intervals for analysis, but short enough for the assumption that intra-group variability is low. It is not necessary that these segments are of the same length or duration; they may or may not overlap and they may or may not use every RR interval available.

In one embodiment, the segments are defined as follows: (1) each segment begins 4 seconds after the previous segment; (2) each segment has a minimum duration of 4 seconds, but can last longer, and thus overlap the next segment, if a sufficient number of RR intervals are not present in the segment (if there are fewer than 6 valid RR intervals in the segment, the segment duration is increased until either 8 valid RR intervals are obtained or a maximum segment length duration of 9 seconds is reached, whichever occurs first) and (3) if the segment still contains less than 4 valid RR intervals, invalidate the segment.

A variability measurement is generated in step 303 for each valid segment obtained in step 301. In order the generate the variability measurement, in step 303a, RR intervals greater than 2 seconds or less than 180 milliseconds are flagged as invalid, as such extreme values are typically caused by heartbeat detection errors. Thus, only RR intervals within the range of 180 milliseconds to 2 seconds are kept. In step 303b, each valid RR interval is converted into an instantaneous heart rate value. In step 303c, the heart rates are sorted into ascending order. In step 303d, the differences between each successive (sorted) heart rate are calculated. The two largest differences are discarded in step 303e. In step 303f, the variability is calculated as the sum of all difference values that have not been discarded (i.e. the range of heart rate values minus the two largest difference values).

In optional step 303g, if there is no valid heart rate value within this particular segment that is greater than 60 beats per minute (a nominal typical human heart rate) then the variability value may be halved.

Additionally, in optional step 303h, the variability value may further be limited if the segment is identified as containing a 'heart rate trend', which is defined in greater detail below. Thus, in step 303, a variability measurement is generated per valid segment.

In order to improve the stability of the measurement at any given time, in step 305, the sequence of segment variability measurements is filtered. Preferably, a 7-sample median filter is used for this purpose, although it should be understood by those of ordinary skill in the art that many other filters would achieve a similar result and thus the use of this particular filter is not to be construed as limiting.

In step 307, the sequence of filtered segment variability measurements are compared to at least one threshold. In one embodiment, both a first threshold and a second threshold are employed: the first threshold is a high threshold to determine if AF is present; the second threshold is a lower threshold to refine the start and end points of any AF event that is found.

In one embodiment, thresholding is achieved as follows: first, each valid filtered segment variability value obtained in step 305 is compared to a first threshold value, which is the AF detection threshold. Then, each valid filtered segment variability value obtained in the first step is compared to a second threshold value, which is the AF start/end threshold. Finally, the total count of segments exceeding the AF start/end threshold is compared to the total count exceeding the AF detection threshold. If the total count of segments exceeding the AF start/end threshold is eight or more times the total count exceeding the AF detection threshold, a "high noise" condition is flagged for this recording. The method of the present invention may optionally incorporate an adaptive threshold: in the event that the high noise state is flagged, both the AF detection and AF start/end thresholds are increased and the values are compared again.

In step 309, if the AF detection threshold is exceeded for a given number of sequential segments then an AF event is declared. In one embodiment, the given number of sequential segments is two. Preferably, segments flagged as having a 'strong trend', as described below, are excluded from this count, though it should be noted that this refinement is optional.

If an AF event has been declared, in step 311, the method of the present invention locates the corresponding comparisons with the AF start/end threshold, and subsequently traces these comparisons backwards and forwards to determine this AF event's start/end points. The AF start/end points are defined where filtered segment variability values have fallen below the start/end threshold.

Referring back to FIG. 3, in step 313, the AF event duration is compared to a threshold to determine if it is a valid AF event. In one embodiment, if the AF event 'duration' (as measured by time, number of segments or number of valid RR intervals) is less than a given threshold, then it is discarded as a false detection; otherwise it is retained as a valid AF event. In one embodiment, the threshold for comparison is 4 valid RR intervals.

Optionally, the use of thresholds can be modified. For example, in one embodiment, and not limited to such example, a single threshold for both AF detection and AF start/end refinement may be used, thus reducing computational load. In another embodiment, additional thresholds may be used. For example, in one embodiment, three thresholds can be used—AF detection threshold, AF start point threshold, and AF end point threshold. The thresholds may be fixed thresholds or adaptive thresholds.

Figure 3:
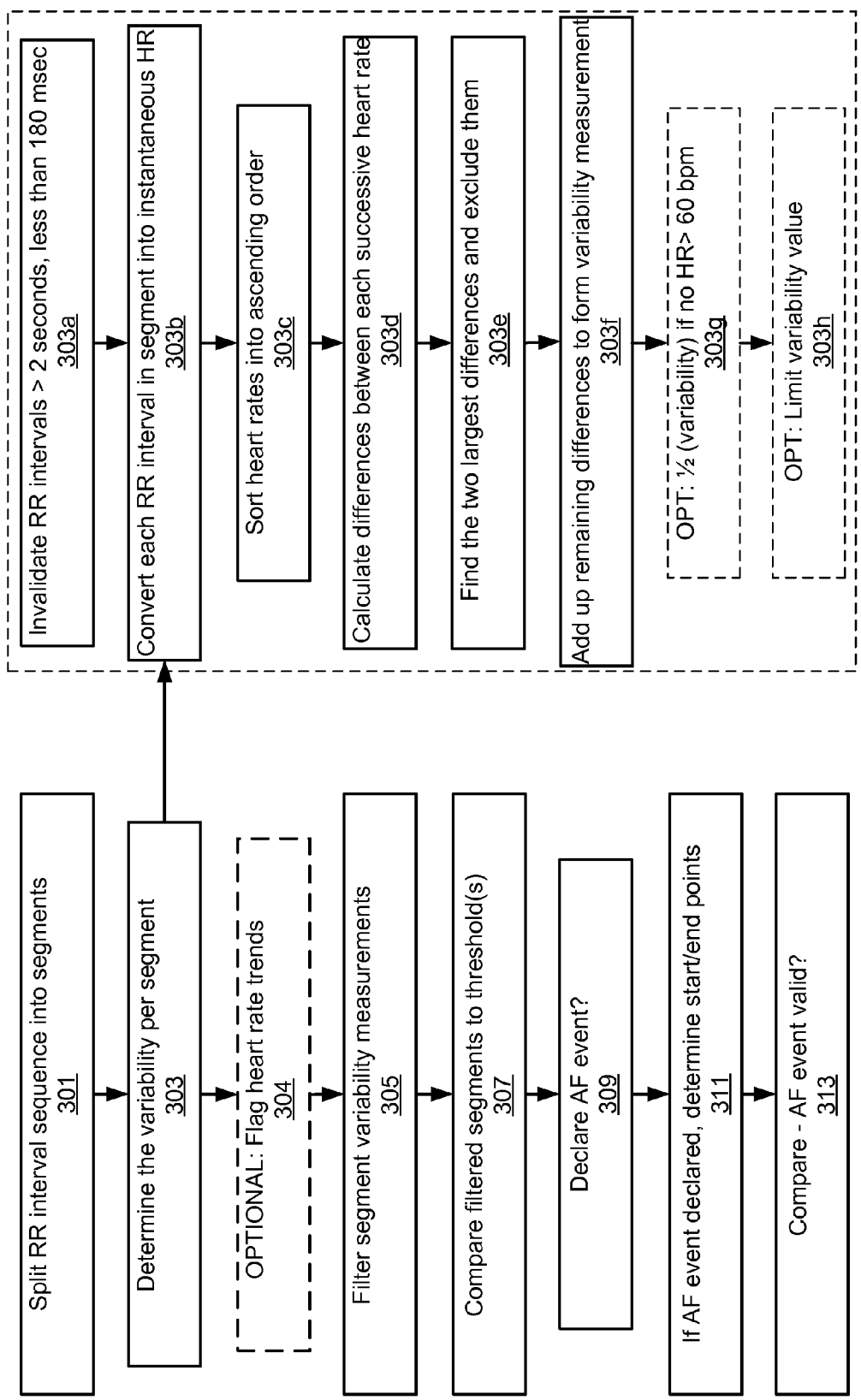
FIG. 3 is a flow chart illustrating general AF detection steps in one embodiment of the method of the present invention.

FIG. 3 illustrates the processing method of the present invention. In one embodiment, additional processing steps may be performed on the collected data to further refine the measurement and further localize AF events. Such optional processing steps are described below. It should be understood to those of ordinary skill in the art that the processing steps described below are not necessary to practice the invention, but rather are additional steps for processing data and are thus not to be construed as limiting.

As described above, AF typically causes the sequence of RR intervals to become chaotic, except in cases where a maximum ventricular rate is achieved during atrial flutter or when complete AV dissociation occurs. A localized very fast change in heart rate however can register as significant variability, even though all heartbeats are due to the same focus. In one optional embodiment, the sequence of instantaneous heart rates is tested for a high degree of order within the heart rate changes in order to avoid false AF detection in regions where the sinus rate varies extremely quickly (an arrhythmia known as "sick sinus syndrome").

Where the heart rate does not change significantly, or changes are consistently in the same direction, a 'heart rate trend' is flagged. While short heart rate trends can occur occasionally within a true AF event, very long trends or a high incidence of trends do not.

A heart rate trend is detected using the following method: For each instantaneous heart rate value, if the heart rate is significantly greater or less than the previous heart rate, then the start of a trend (of either increasing or decreasing rate) is defined. In one embodiment, "significantly" is defined as a difference greater than 5 beats-per-minute or 4% of the current heart rate, whatever is the greater, although various other definitions may be used.

If the number of valid heart rates in a trend exceeds a "long threshold", each heart rate in that trend is flagged as being a member of a long heart rate. In one embodiment, a 'long threshold' is defined as 12 valid heart rates. Similarly, if the number of valid heart rates in a trend exceeds only a lower "short threshold", then each heart rate in that trend is flagged as being a member of a short heart rate. In one embodiment, a 'short threshold' is defined as 5 valid heart rates.

For each segment, the relative incidence of trend flags is tested to establish whether that segment is dominated by heart trend behavior. In one embodiment, each long trend interval is assigned a count of +1, each short trend interval is assigned a count of 0, and all non-trended intervals are assigned a count of −1. If the average count is less than zero, the segment is flagged as having "no trend". If the average count is greater than 0.5, it is flagged as being "strongly trended". If the average count is in the range of 0 and 0.5, it is flagged as having unknown trend status.

In one embodiment, segment trend flags are employed when calculating each segment's variability measurement, shown in FIG. 3 as optional step 304, before filtering the sequence of variability measurements. Any segment with a strong trend has its variability value set to zero, as the trend indicates that this variability is very structured and thus not relevant to AF detection. Each segment trend with the "unknown" trend status has its segment variability halved, as there is a suspicion of structured variability, rather than chaotic variability. Segments flagged with "no trend" are left as initially calculated.

In addition, when declaring an AF event, the individual heart rate trend flags within that event are collected and summed, again using each long trend interval as a count of +1, each short trend as a count of 0 and all non-trended intervals as −1. If the average count over the AF event is greater than a given threshold, then the AF event is discarded as being a false detection. In one embodiment, the given threshold value is −0.25.

In another optional embodiment of the present invention, the sequence of NN intervals is used instead of the sequence of RR intervals when generating the variability measurement, when such information is available. Typically, most measurement devices are not capable of providing a true definition of a beat being of sinus origin: thus, in one embodiment, an NN* interval is defined as an interval that is surrounded by two consecutive non-ventricular beats. Thus NN* intervals differ from NN intervals in that NN* intervals include SVEs in addition to sinus beats. Using NN* intervals suppresses some, though not all, of the commonly encountered ectopy that might influence the measurement of variability. It should be understood by those of ordinary skill in the art that this embodiment can only be implemented if the device generating the sequence of heartbeat detections is capable of differentiating heartbeats of ventricular origin from those of non-ventricular origin. If the particular device cannot, the method reverts back to using RR intervals as previously described with respect to FIG. 3.

The AF detection methods of the present invention can have some dropouts during a true AF episode, thus causing a single AF event to be detected as several separate episodes. In order to counter this, in an optional embodiment, when two AF events are in close proximity, they are merged together into a single event if the following two conditions are met: (1) the AF events are separated by less than 30 seconds and (2) the region between the two AF events contains no strong heart rate trends.

In one embodiment, strong heart rate trends are employed to refine start/end intervals of the detected AF events. Optionally, the AF onset time may be modified by looking forward from the start time of the AF event to the closer of either the start time of the AF event plus 8 intervals or the end of the AF event. Once the closer of the two points is identified, trace backwards to a maximum of 8 intervals preceding the AF event, looking for a strong heart rate trend. If a strong heart rate trend is identified, the AF start point is redefined as immediately following that interval.

The end point is similarly modified, in the opposite search direction, only if the heart rate falls after the end of the AF event. If the heart rate does not fall, then the end region is checked for local atrial flutter, which can terminate AF detection by causing the maximum ventricular rate to occur, thus suppressing ventricular variability during AF. "Hidden AF", as it is termed, is determined by extending the AF event if the following conditions are met: (a) the heart rate before the start of the AF event is less than 120 beats per minute (b) the heart rate at the end of the initially detected AF event is greater than 90 beats per minute and (c) the rate after the end of the event remains more than an end threshold given by either 15 beats per minute less that the rate at the end of the event or 10 beats per minute greater than the rate before the start of the event, whichever is the greater. When hidden AF is indicated, the AF event is extended until the rate falls to below the end threshold of (c) or a majority of local intervals become either non-sinus or invalid.

After the end point is detected (and optionally adjusted), if the AF event contains fewer than six valid intervals, the AF event is discarded as being too short for a reliable detection to be made.

The present invention of AF measurement and detection is applicable to any signal processing methods that use heart rate variability or RR or NN interval variability data. The above examples are merely illustrative of the many applications of the methods of the present invention. Although only a few embodiments of the present invention have been described herein, it should be understood that the present invention might be embodied in many other specific forms without departing from the spirit or scope of the invention. For example, while the methods above are directed towards the detection of AF events, other irregular cardiac events (such as, though not limited to, Ventricular Flutter) may be processed using similar methods and thus detected.

The invention claimed is:

1. A system for calculating a variability value that is indicative of AF using a sequence of RR intervals, wherein said system comprises a non-volatile computer readable medium storing a plurality of programmatic instructions and wherein said programmatic instructions, when executed:
   obtain a signal sequence comprising a plurality of RR intervals wherein said signal sequence is obtained by monitoring the time intervals between successive heart beats of a patient's heart by measuring at least one of electrical activity; acoustic activity; trans-thoracic impedance; blood pressure; blood velocity; blood oxygenation; heart movement and/or deformation;
   convert each RR interval in said sequence into an instantaneous heart rate value;
   sort said instantaneous heart rate values into ascending order;
   calculate differences between each of said sorted successive instantaneous heart rates;
   discard two largest differences generated in the previous step; and
   calculate a variability value by adding differences which were not discarded.

2. The system of claim 1, wherein said programmatic instructions, when executed, also segment said RR interval sequence into a plurality of segments and generate a variability value for each said segment.

3. The system of claim 2, wherein said programmatic instructions, when executed, also filter said generated variability value for at least one segment using previous or successive segment variability values.

4. The system of claim 3 wherein said filtering is implemented by a 7-sample median filter.

5. The system of claim 2, wherein said programmatic instructions, when executed, compare at least one said variability value to at least one threshold.

6. The system of claim 5 wherein said comparing of at least one said variability value to at least one threshold comprises comparing at least one said variability value to an AF detection threshold or an AF start/end threshold.

7. The system of claim 6, wherein after said comparing at least one said variability value to at least one threshold, a corresponding segment is flagged as 'probably containing AF' when said detection threshold is exceeded and an AF event is detected when a pre-determined number of consecutive segments are flagged as 'probably containing AF' and a corresponding segment is flagged as 'AF extension permitted' when said start/end threshold is exceeded.

8. The system of claim 7, wherein once an AF event has been detected, previous and/or following segments are tested for the AF extension permitted flag and, if found, the detected AF event is extended to include said segment(s).

9. The system of claim 1 wherein RR intervals shorter than 180 milliseconds or longer than 2 seconds are discarded from the variability calculation.

10. The system of claim 1, wherein said programmatic instructions, when executed, reduce said variability value if said sequence contains no heart rate interval greater than a heart rate threshold.

11. The system of claim 10 wherein said heart rate threshold is 60 beats per minute.

12. The system of claim 10 wherein said reduction is implemented by halving said variability value.

13. The system of claim 1, wherein said programmatic instructions, when executed, limit said variability value if said sequence is identified as containing a heart rate trend.

14. The system of claim 13 wherein said heart rate trend is identified by, for each instantaneous heart rate of an RR interval, if the heart rate is significantly greater or less than the previous interval heart rate, defining the start of a trend.

15. The system of claim 14 wherein a trend is determined to persist until an RR interval with a significant heart-rate change in an opposite direction is detected.

16. The system of claim 15 wherein, once a new trend is determined on a RR interval, all intervals in a previous trend are flagged as being of the previous trend type.

17. The system of claim 16 wherein each RR interval in a trend is flagged as being a member of a long heart rate if a consecutive number of RR interval trend flags exceeds a long heart rate threshold.

18. The system of claim 17 wherein each RR interval in a trend is flagged as being a member of a short heart rate if a consecutive number of RR interval trend flags exceeds a lower short heart rate threshold.

19. The system of claim 18 wherein each RR interval in a trend is flagged as being not trended if no threshold conditions apply.

20. The system of claim 19 where, for a plurality of RR intervals, trend flags are tested to establish whether said plurality is dominated by heart trend behavior.

21. The system of claim 20 wherein said testing is performed by assigning each long heart rate trend flag a count.

22. The system of claim 21 wherein said testing is performed by assigning each short heart rate trend flag a count less than said count of the long heart rate trend flag.

23. The system of claim 22 wherein said testing is performed by assigning each non trend flag a count less than said count of the short heart rate trend flag.

24. The system of claim 23 wherein an average of said long heart rate trend count, short heart rate trend count, and non-trend count is taken.

25. The system of claim 24 wherein if said average is below a first threshold, said plurality of RR intervals is determined to have no trend.

26. The system of claim 25 wherein if said average is greater than a second threshold, said plurality of RR intervals is determined to have a strong trend.

27. The system of claim 26 wherein if said average is between said first and said second thresholds, said plurality of RR intervals is determined to have an unknown trend.

28. The system of claim 15 wherein significantly is defined as a difference greater than 5 beats-per-minute or 4% of the current heart rate.

29. The system of claim 8, further comprising the step of validating each detected AF event.

30. The system of claim 29 wherein said step of validating each detected AF event comprises assigning individual trend flags within that event, summing individual trend flags, and discarding the AF event as false detection where the average count over the AF event is greater than a predefined threshold.

31. A system for calculating a variability value that is indicative of AF using a sequence of NN intervals, wherein said system comprises a plurality of programmatic instructions that, when executed:
   obtain a signal sequence comprising a plurality of NN intervals wherein said signal sequence is obtained via monitoring the time intervals between successive heart beats of a patient's heart by measuring and analyzing at least one of electrical activity; acoustic activity;

trans-thoracic impedance; blood pressure; blood velocity; blood oxygenation; heart movement and/or deformation;

convert each NN interval in said sequence into an instantaneous heart rate value;

sort said instantaneous heart rate values into ascending order;

calculate differences between each of said sorted successive instantaneous heart rates;

determine two largest differences of said calculated differences;

discard said two largest differences, thereby leaving a plurality of retained differences; and calculate a variability value by adding the retained differences.

* * * * *